(12) United States Patent
Ghiasvand et al.

(10) Patent No.: US 10,315,934 B2
(45) Date of Patent: Jun. 11, 2019

(54) QUANTUM DOT-BASED FILTER

(71) Applicants: Alireza Ghiasvand, Khoramabad (IR); Samira Koonani, Koohdasht (IR); Fatemeh Yazdankhah, Khoramabad (IR); Saeid Farhadi, Khoramabad (IR)

(72) Inventors: Alireza Ghiasvand, Khoramabad (IR); Samira Koonani, Koohdasht (IR); Fatemeh Yazdankhah, Khoramabad (IR); Saeid Farhadi, Khoramabad (IR)

(*) Notice: Subject to any disclaimer, the term of this patent is extended or adjusted under 35 U.S.C. 154(b) by 70 days.

(21) Appl. No.: 15/687,336

(22) Filed: Aug. 25, 2017

(65) Prior Publication Data

US 2018/0037472 A1    Feb. 8, 2018

(30) Foreign Application Priority Data

Aug. 25, 2016    (IR) .................. 13955014000300674

(51) Int. Cl.
| | | |
|---|---|---|
| C02F 1/28 | (2006.01) | |
| B01D 15/10 | (2006.01) | |
| G01N 1/14 | (2006.01) | |
| G01N 1/34 | (2006.01) | |
| B01J 20/22 | (2006.01) | |
| G01N 1/40 | (2006.01) | |
| C02F 101/32 | (2006.01) | |

(52) U.S. Cl.
CPC .............. *C02F 1/281* (2013.01); *B01D 15/10* (2013.01); *B01J 20/223* (2013.01); *C02F 1/288* (2013.01); *G01N 1/14* (2013.01); *G01N 1/34* (2013.01); *G01N 1/405* (2013.01); *C02F 2101/327* (2013.01); *G01N 2001/4088* (2013.01)

(58) Field of Classification Search
CPC ......... C02F 1/281; C02F 1/288; G01N 1/405; G01N 1/34; G01N 1/14; B01J 20/223; B01D 15/10
See application file for complete search history.

(56) References Cited

U.S. PATENT DOCUMENTS

| | | | |
|---|---|---|---|
| 6,869,864 B2 | 3/2005 | Yim | |
| 7,005,669 B1 | 2/2006 | Lee | |
| 7,309,372 B2 | 12/2007 | Kahbaugh | |
| 7,867,556 B2 | 1/2011 | Pickett | |
| 2004/0253624 A1 | 12/2004 | Smith | |
| 2012/0267321 A1* | 10/2012 | Kisailus | ................... C01G 1/00 210/748.09 |
| 2016/0158738 A1* | 6/2016 | Ozaki | ...................... B01J 35/02 502/159 |
| 2017/0014815 A1* | 1/2017 | Ozaki | ...................... B01J 31/28 |
| 2017/0327389 A1* | 11/2017 | Kisailus | ................... C02F 1/325 |
| 2018/0036719 A1* | 2/2018 | Wu | ............................ A61L 9/22 |
| 2018/0147572 A1* | 5/2018 | Fukumura | ............ B01J 20/3214 |
| 2018/0355200 A1* | 12/2018 | Banin | .................... B33Y 70/00 |

\* cited by examiner

*Primary Examiner* — Chester T Barry
(74) *Attorney, Agent, or Firm* — NovoTechIP International PLLC

(57) ABSTRACT

A filter device and method for making the device is disclosed. The filter device can include a chemical filtration disk in which QDs (QD) are deposited. In one example, cadmium sulfide (CdS) is combined with trioctylphosphine oxide (TOPO) to form a CdS-TOPO QDs sorbent that is arranged on an ODS disk. The method of fabricating the device is presented, as well as its many benefits.

20 Claims, 18 Drawing Sheets

| Analytes | LDR (μg·mL$^{-1}$) | Equation | R$^2$ | RSD%(n=6) | LOD (ng·mL$^{-1}$) |
|---|---|---|---|---|---|
| Nap | 0.0020-1 | Y=6358.8x+2916.7 | 0.9897 | 5.0 | 0.0005 |
| Ace | 0.00010-1 | Y=15093x+31113 | 0.9864 | 6.9 | 0.0001 |
| Flr | 0.0025-2 | Y=9483.5x-5764.5 | 0.9933 | 7.4 | 0.005 |
| Ant | 0.0010-2 | Y=12917x-4569.7 | 0.9848 | 9.9 | 0.0025 |
| Flt | 0.0065-2 | Y=7007.8x-1732.8 | 0.9986 | 6.7 | 0.0015 |
| Pyr | 0.006-1 | Y=8230x-8835.1 | 0.9857 | 9.3 | 0.001 |

FIG. 11A

| Sample | Added (µg mL⁻¹) | QD-SPE-GC-FID method | | | | | | |
|---|---|---|---|---|---|---|---|---|
| | | Nap | Ace | Flr | Ant | Flt | Pyr |
| Water 1 | 0 | NF | NF | NF | NF | NF | NF |
| | 0.1 | 0.09(7.8) | 0.092(7.7) | 0.087(6.3) | 0.108(5.7) | 0.089(10.1) | 0.11(6.3) |
| Water 2 | 0 | 0.0043(10) | 0.0058(11.3) | 0.002(9.7) | NF | NF | NF |
| | 0.1 | 0.0914(9.1) | 0.1007(8.9) | 0.111(8.5) | 0.09(7.9) | 0.088(8.5) | 0.103(8.8) |
| Water 3 | 0 | 0.064(6.1) | 0.051(9.6) | 0.055(7.3) | 0.07(9.4) | 0.02(7.6) | 0.01(5.9) |
| | 0.1 | 0.176(8.4) | 0.163(10.7) | 0.161(11.2) | 0.16(8.9) | 0.138(9.2) | 0.099(9.6) |

FIG. 11C

QUANTUM DOT-BASED FILTER

CROSS-REFERENCE TO RELATED APPLICATION

This application claims the benefit of priority from Iranian Patent Application Serial Number 139550140003006745, filed on Aug. 25, 2016, and entitled "Solid Phase Extraction Disk Using Quantum Dots," the content of which is incorporated herein by reference in its entirety.

TECHNICAL FIELD

The present disclosure generally relates to measurement and filtering systems, and more particularly to filters for polycyclic aromatic hydrocarbons, and a method for fabricating such filtering systems.

BACKGROUND

Polycyclic aromatic hydrocarbons (PAHs) are organic pollutants that are widely found in the environment. They may be found in air attached to dust particles, soil, sediments, water and food. Most PAHs enter the environment during burning of most organic materials such as coal, oil, wood, gasoline, garbage, tobacco, and petroleum. They are an important class of environmental contaminants because of their potential adverse health effects. They are known to have carcinogenic, mutagenic and teratogenic properties.

Different water sources can be contaminated with PAHs from dry and wet deposition, road runoff, industrial waste water and petroleum spills. In addition, different extraction techniques have been applied for extracting PAHs from water samples from sea, rivers, lakes, surface, ground, industrial waste and drinking water. However, such techniques require large sample sizes and can be prohibitive in cost, making the extraction process challenging. Therefore, there is a need in the art for a simplified, economical method for measuring and extracting contaminants with high accuracy that requires only a small sample size.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure is directed to a method for fabricating a solid-phase extraction disk. The method includes combining carbon disulfide with cadmium nitrate in a first solvent, thereby forming a first mixture, and producing cadmium sulfide (CdS) from the first mixture. The method also includes adding trioctylphosphine oxide (TOPO) to the produced cadmium sulfide, thereby forming cadmium sulfide-trioctylphosphine oxide (CdS-TOPO) quantum dots (QDs), mixing the CdS-TOPO with a second solvent to obtain a CdS-TOPO suspension, and adding the CdS-TOPO mixture to a piece of an octadecyl silica (ODS) disk to stabilize CdS-TOPO QDs on it and to form a chemical filtration disk.

The above general aspect may include one or more of the following features. The method can also include heating the first mixture at a high temperature and obtaining a resultant powder, and/or washing and drying the resultant powder to obtain the CdS-TOPO QDs. In some implementations, the method can include inserting the ODS disk into a syringe, mixing the CdS-TOPO QDs with a second solvent to obtain a second mixture, and/or passing the second mixture through the syringe repeatedly until a first amount of the second mixture is deposited on a surface of the ODS disk. In some cases, the ODS disk can be washed with water and/or methanol. In addition, in one implementation, the method involves washing the filtration disk in order to clear away excess CdS-TOPO disposed on the disk, and/or drying the chemical filtration disk. In another implementation, the ODS disk is disposed between a pre-filter and a disk support. Furthermore, in some cases, the ODS disk, pre-filter, and disk support are arranged in a housing that includes a connector portion configured to facilitate a connection with the syringe.

In another general aspect, the present disclosure is directed to a chemical filtration apparatus for extraction of PAHs. The apparatus includes a filter device, the filter device including a solid-phase extraction (SPE) disk, as well as a sorbent disposed on a surface of the SPE disk, where the sorbent includes a combination of quantum dot particles and a stabilizing agent.

The above general aspect may include one or more of the following features. In some cases, the apparatus includes a filtration unit, where the filtration unit includes housing and the filter device is located within the housing. As another example, the apparatus may include a syringe, and the filtration unit is connected to the syringe. In some implementations, the filter device further includes a pre-filter disk, where the SPE disk is positioned adjacent to the pre-filter disk. In other implementations, the filter device may include a disk support, where the SPE disk is positioned between the pre-filter disk and the disk support. In one example, the SPE disk includes an ODS disk, the quantum dot particles include cadmium sulfide (CdS), and/or the stabilizing agent includes trioctylphosphine oxide (TOPO). The above general aspect may include one or more of the following features.

In another general aspect, the present disclosure is directed to a method for extraction of PAHs. The method includes assembling a filter device, the filter device including a SPE disk covered with quantum dot particles and a stabilizing agent, and drawing a sample fluid containing PAHs into a syringe. The method further includes attaching a filtration unit to a syringe, the filtration unit including the filter device, and passing the sample solution through the filter device.

The above general aspect may include one or more of the following features. In some cases, the SPE disk includes an ODS disk. Furthermore, as an example, the quantum dot particles can include cadmium sulfide. In another example, the stabilizing agent can include trioctylphosphine oxide.

Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the following claims.

BRIEF DESCRIPTION OF THE DRAWINGS

The drawing figures depict one or more implementations in accord with the present teachings, by way of example

FIGS. 11A-11C present the method validation results for analysis of PAHs from aqueous samples, according to an implementation of the present disclosure;

DETAILED DESCRIPTION

Figure 1:
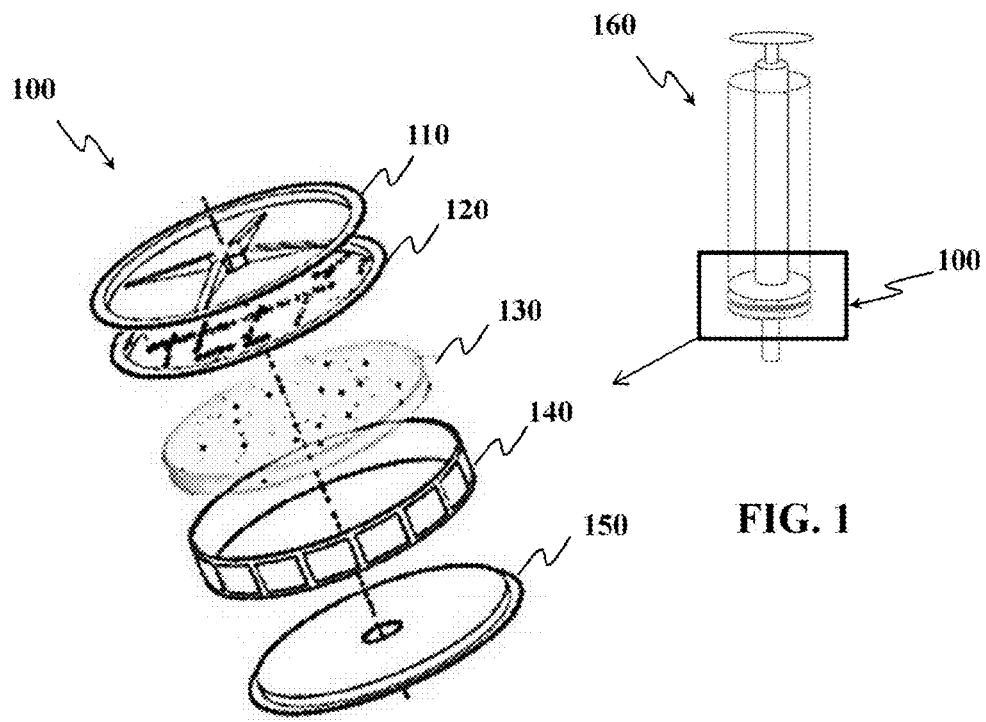
FIG. 1 is a schematic illustration of an implementation of an apparatus for solid-phase extraction, of hydrocarbons.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is, presented to enable a person skilled in the art to make and use the methods and devices disclosed in exemplary implementations of the present disclosure. For purposes of explanation, specific nomenclature is set forth to provide a thorough understanding of the present disclosure. However, it will be apparent to one skilled in the art that these specific details are not required to practice the disclosed implementations. Descriptions of specific exemplary implementations are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

As noted above, different extraction techniques have been applied for extracting PAHs from water or other fluid-based samples. The following disclosure presents an improved and cost-effective technique for the separation, extraction, and measurement of PAHs from a fluid. This further includes a discussion related to the design, production, and modification to a type of solid-phase extraction (SPE) disk using Quantum Dots (QDs). Thus, in the following description, a filter device and method for making the device is described in which a chemical filtration disk includes QDs.

For purposes of this disclosure, quantum dots are very small semiconductor particles, typically several nanometers in size, and so small that their optical and electronic properties differ from those of larger particles. Such nanoscale semiconductor materials tightly confined either electrons or electron holes. Quantum dots are also sometimes referred to as artificial atoms, a term that emphasizes that a quantum dot is a single object with bound, discrete electronic states, as is the case with naturally occurring atoms or molecules. Quantum dots exhibit properties that are intermediate between those of bulk semiconductors and those of discrete molecules. Their optoelectronic properties change as a function of both size and shape. Larger QDs (5-6 nm, for example) emit longer wavelengths resulting in emission colors such as orange or red. Smaller QDs (2-3 nm, for example) emit shorter wavelengths resulting in colors like blue and green, although the specific colors and sizes vary depending on the exact composition of the QD. The processing techniques associated with QDs may result in less-expensive and less time consuming methods of semiconductor fabrication. QDs can be made of binary compounds such as lead sulfide, lead selenide, cadmium selenide, cadmium sulfide, indium arsenide, indium phosphide, and other such compounds. For example, QDs may also be made from ternary compounds such as cadmium selenide, or sulfide silicon and/or germanium. Such QDs can contain as few as 100 to 100,000 atoms within the quantum dot volume, with a diameter of approximately 10 to 50 atoms.

The implementations described below make use of QDs to provide a specialized filtration membrane that can effectively trap and/or extract hydrophobic molecules. In one implementation, the QDs can be combined with extraction or stabilizing agent and be arranged on a substrate disk to form a chemical filtration disk. As described herein, the chemical filtration disk can be utilized to provide an improved alternative to other filtration and extraction tools for various contaminants. In some implementations, the filtration disk is used to measure and/or extract PAHs (such as, for example, petroleum emitted compounds) and other polluting agents from fluids. This specialized system generally requires shorter times, smaller amounts of fluid as sample size, and fewer materials, relative to the conventional systems such as liquid-liquid extraction (LLE) and Soxhlet.

When applied to a substrate disk and used in chemical filtration, QDs increased the efficiency of extraction, as will be illustrated further below. This is due at least in part to the high active surface of the quantum dots. In one implementation, a disk with ODS is modified with cadmium sulfide quantum dots, providing a filtration disk with sensitive and selective extraction of polycyclic aromatic hydrocarbons (PAHs) from polluted water samples. To achieve maximum extraction efficiency, influential parameters like the type, volume, flow rate of eluent used, as well as the amount of absorbent used were tested and, optimum parameters were identified.

As a general overview, the following disclosure presents a powerful filtration apparatus utilizing SPE based on quantum dots. As will be discussed in detail below, in some implementations, the device includes a SPE disk or wafer and two protecting surfaces, as well as an especial SPE syringe. In some cases, the SPE disk can be disposed between surfaces including polytetrafluoroethylene (PTFE) or Teflon™.

Furthermore, in some implementations, cadmium sulfide QDs is added to the SPE disk. In one implementation, the QDs is synthesized using a hydrothermal method. The hydrothermal method can help ensure that the QDs particles are substantially unified or consistent in their characteristics. In addition, in one implementation, the size of the QDs particles used is in the order of 10 nm, though in other implementations, the size can range between 2-15 nm.

In order to increase the stability and durability of the QDs they can be combined or covered with trioctylphosphine oxide (TOPO) or other stabilizing agents. The TOPO can be used to physically fix or attach the QDs onto the disk. The disk (modified with CdS-TOPO) can be fixed between two Teflon layers and placed at the end of the especial SPE syringe for use in extraction of PAHs.

As used herein the term "polycyclic aromatic hydrocarbon" or "PAH" refers generally to aromatic hydrocarbon molecules containing two or more six-membered rings, two or more five-membered rings or a mixture of one or more five- and one or more six-membered rings. For example, PAHs can have one aromatic six-member ring and a saturated or unsaturated six-member or five-member ring (e.g., indene and indane); two aromatic rings (e.g., naphthalene); and three aromatic rings (e.g., anthracene and phenanthrene). The term "PAH" excludes fullerenes and other carbon nanomaterials. Typically PAHs are components of combustion soot produced by the combustion of hydrocarbon fuels during the production of fullerenes. The term "PAH" is intended to encompass all such molecules produced during the formation of combustion soot and is not intended to be limited to specific members of the general class of molecules.

Furthermore, it should be understood that as used herein the term "substantially soluble" refers to the solubility of a material in a solvent and particularly to materials that are soluble in a specific solvent, solvent mixture, or class of solvents. Conversely, the term "not substantially soluble" refers to a situation where a particular material does not dissolve in a solvent or sparingly dissolves, such that further processing steps are feasible and recovery yields are acceptable.

Furthermore, as used herein the verb "extracting" refers to using a solvent to remove one or more components from a mixture by contacting the mixture with the solvent. Extraction can be a single or multi-step process. Extractions most generally can be liquid-liquid extraction (LLE) or solid-phase extraction (SPE). In the present invention, solid-phase extraction (or solid-liquid extraction) is typically used. In a LLE process a mixture in liquid form, e.g., a mixture of solutes in a solvent is extracted with a liquid solvent. A solution of solutes is extracted with a second solvent typically to separate one or more of the solutes by extraction into that second solvent. In this case, the solvent used to dissolve the solutes is generally not soluble in the second solvent. In SPE, a solid material, having a mixture of components, which may be a dried extract from which solvent has been removed, is contacted with a solvent to remove or separate one or more mixture components from the other components. In selective extraction, selected components are removed from the mixture. As used herein "washing" is a form of extraction in which the mixture has brief exposure to the solvent, typically to minimize undesired solubilization of a component.

In addition, as used herein, the noun "extract" refers to a substance obtained by using a solvent to remove one or more components from a mixture. The extracts formed in the present invention (e.g. combustion soot extract) are typically concentrated to substantially remove the solvent prior to further extraction. Suitable methods for concentrating solutions are known to those skilled in the art. However, it is preferred to use temperatures and pressures which will not cause substantial sublimation of the carbon nanomaterial(s) of interest.

Similarly, as used herein, the term "purification" refers to the removal of impurities from, a substance. As used herein the term "continuous purification" or "continuous extraction" generally refers to a process or method wherein impurities are removed from a sample without the intervention of additional process steps. An example of a continuous purification technique is Soxhlet extraction. The carbon nanomaterials, including fullerenes, treated by the method of the present invention to remove undesired impurities are typically mixtures of components. As used herein the term "purification" does not typically refer to the generation of a single component product. As used herein, the term "purity" refers to the extent of being pure, where a pure material contains no detectable undesired component (i.e., impurity). In the present disclosure, pure materials or purified materials typically contain a mixture of components. e.g., a mixture of different carbon nanomaterials, from which some or most preferably all detectable undesired impurities are removed. In the present disclosure, it is, particularly desired to remove PAHs from a sample.

Referring first to FIG. 1, a chemical filtration apparatus ("apparatus") 160 is shown. In different implementations, the apparatus 160 can include a syringe, tube, barrel, plunger, piston, cylindrical container, vessel, and/or other components. Furthermore, the syringe can be associating with a filter device 100. As shown in the exploded view of an implementation of the filter device 100, the filter device 100 can include various components, portions, and/or sections. As shown in FIG. 1, the filter device 100 includes a filtering system that includes a pre-filter disk ("pre-filter") 120, a filter disk 130, and a disk support 150. In some implementations, the filtering system can be contained, stored, held, assembled, or otherwise covered by or within the housing. In one implementation, the housing can include an upper portion 110 and/or a casing 140. In other implementations, there may be no housing, or the housing can differ from that shown in FIG. 1. For example, in some implementations, the filtering system can be connected or attached together without the housing and be directly inserted within a syringe. Thus, in some implementations, the housing includes provisions for direct connection to a syringe (see FIG. 9).

In different implementations, the pre-filter 120 can be used to clarify small volumes of fluid or highly viscous solutions and/or remove large particulates from suspensions. Thus, the pre-filter 120 can be made of any material configured to act as a filter known by those skilled in the art, such as polypropylene fiber, glass microfiber media, nylon, polyether sulfone (PES), polyvinylidene fluoride (PVDF), polytetrafluoroethylene (PTFE), mixed cellulose (MCE), membrane filtration, and/or other materials that can provide preliminary sample filtration.

In some implementations, the pre-filter 120 is disposable. In other implementations, the pre-filter 120 may be reusable. Furthermore, in different implementations, the pre-filter 120 may include a substantially similar shape and size or area relative to the filter disk 130. In addition, when the components of the filter device are assembled and/or stacked, the pre-filter can be substantially aligned with the filter disk. In one implementation, a lower surface of the pre-filter directly faces, contacts and/or is disposed flat or flush against an upper surface of the filter disk. In still other implementations, an additional material may be positioned between the pre-filter and the filter disk to facilitate the secure placement of the components, and/or to promote improved filtering.

The filter device 100 can further include the disk support 150. In different implementations, the disk support 150 can include a substantially rigid or inelastic material configured to provide support and strength to the filter disk 130. In addition, the disk support 150 may include a substantially similar shape and size or area relative to the filter disk 130. Furthermore, when the components of the filter device are assembled and/or stacked, the disk support can be substantially aligned with the filter disk. In one implementation, a lower surface of the filter disk directly faces, contacts and/or is disposed flat or flush against an upper surface of the disk support. Thus, in some cases, the disk support 150 is disposed directly beneath the filter disk 130, while the pre-filter 120 is disposed directly above the filter disk 130, providing a kind of "sandwiched" system. However, it should be understood that in other implementations, the filter device may not include a disk support, or there may be an additional material layer between the filter disk 130 and the disk support 150 to facilitate secure placement of the components, to improve the fit of the components in the system, and/or to improve the filtering process.

Figure 2:
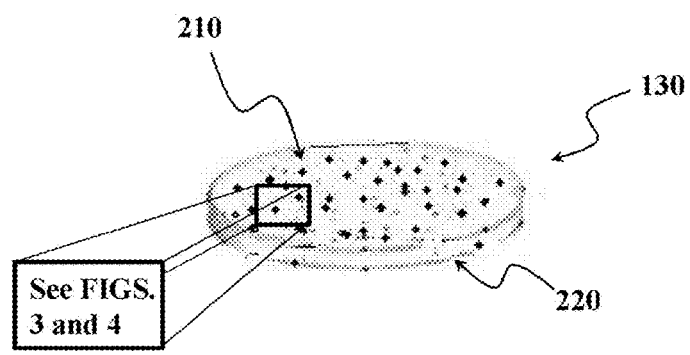
FIG. 2 is a schematic illustration of an implementation of a component used in the extraction of hydrocarbons.

In order to better describe the apparatus to the reader, FIG. 2 illustrates a magnified, isometric view of the CdS-TOPO QDs chemical filtration disk 130 if FIG. 1. It can be seen that in some implementations, the filter disk 130 has a substantially round cross-sectional shape in a horizontal plane. The filter disk 130 can have a substantially cylindrical three-dimensional shape with a thickness smaller than the diameter. However, in other implementations, the shape of the filter disk 130 can vary depending on the specifications of the syringe or overall filtration system being used, the type of housing, and/or the desired filtration, and have any other regular or irregular shape.

As will be discussed further below with respect to FIG. 8, the filter disk 130 can include various elements arranged on or in a substrate. In particular, the filter disk 130 can hold a filtration composition of CdS-TOPO QDs. In FIG. 2, the filter disk 130 includes a filtration composition 210 arranged on a substrate 220. Referring to FIGS. 3A-3D, additional detail regarding the filtration composition 210 is illustrated by way of a series of four SEM images.

Figure 3A:
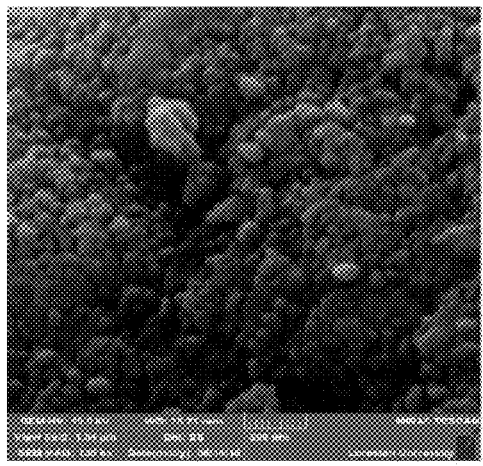
FIGS. 3A-3D are a series of scanning electron microscope (SEM) images of a cadmium sulfide-trioctylphosphine oxide mixture according to an implementation of the present disclosure.
Figure 3B:
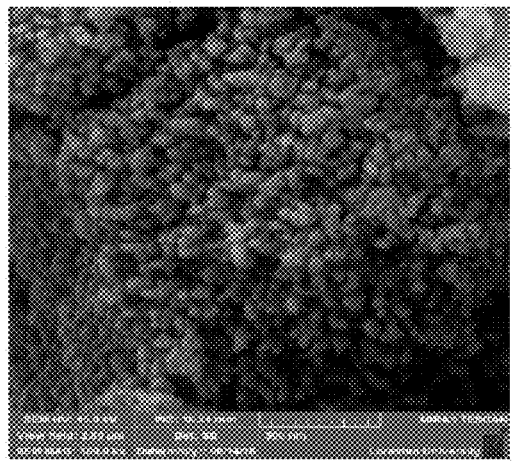
Figure 3C:
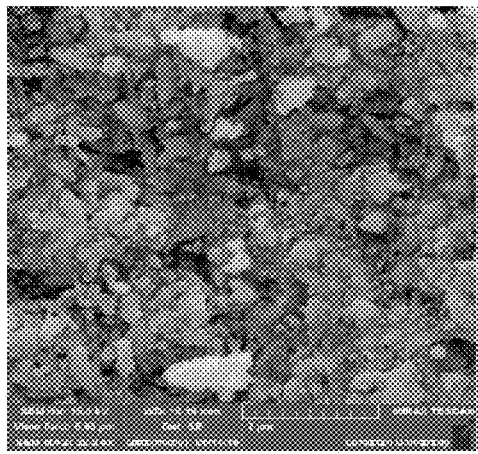
Figure 3D:
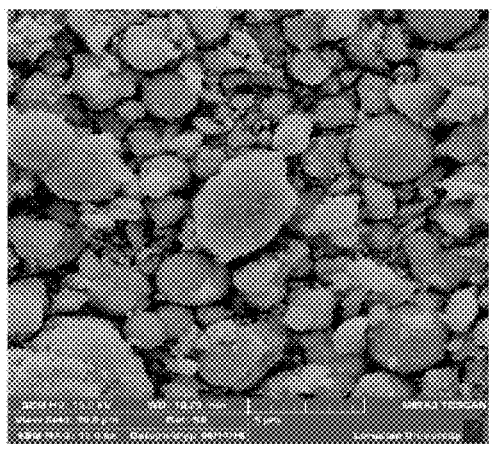

In the first SEM image of FIG. 3A, the filtration composition on the surface of the substrate shown in FIG. 2 is magnified at a first magnification level of approximately 200 nm, and in the second SEM image of FIG. 3B at a second magnification level of approximately 500 nm. In addition, the third SEM image of FIG. 3C is magnified at a third magnification level of approximately 2 µm, and at a fourth magnification level of approximately 5 µm in FIG. 3D. The composition in these images includes a CdS-TOPO QDs sorbent. In the four SEM images the QDs (CdS) and TOPO sorbent are bonded via chemical attractions. For example, the piece of ODS membrane contains $C_8$ groups and the TOPO includes $C_{18}$ alkyl chains that attract one another and allow the composition to gel together. This can provide an active, porous surface for the trapping and/or extracting of hydrophobic compounds. The CdS and TOPO has been combined to provide a kind of powdered substance on the substrate, and clustered together to form a specialized filtration matrix.

Figure 4A:
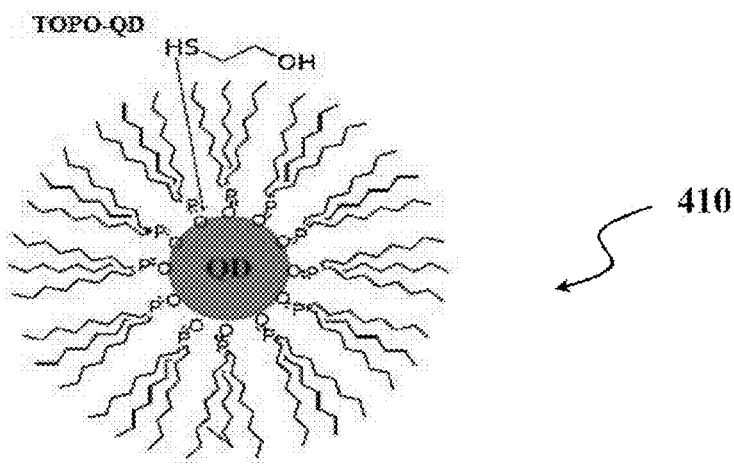
FIGS. 4A and 4B are two schematic illustrations of the cadmium sulfide-trioctylphosphine oxide quantum dots structure.
Figure 4B:
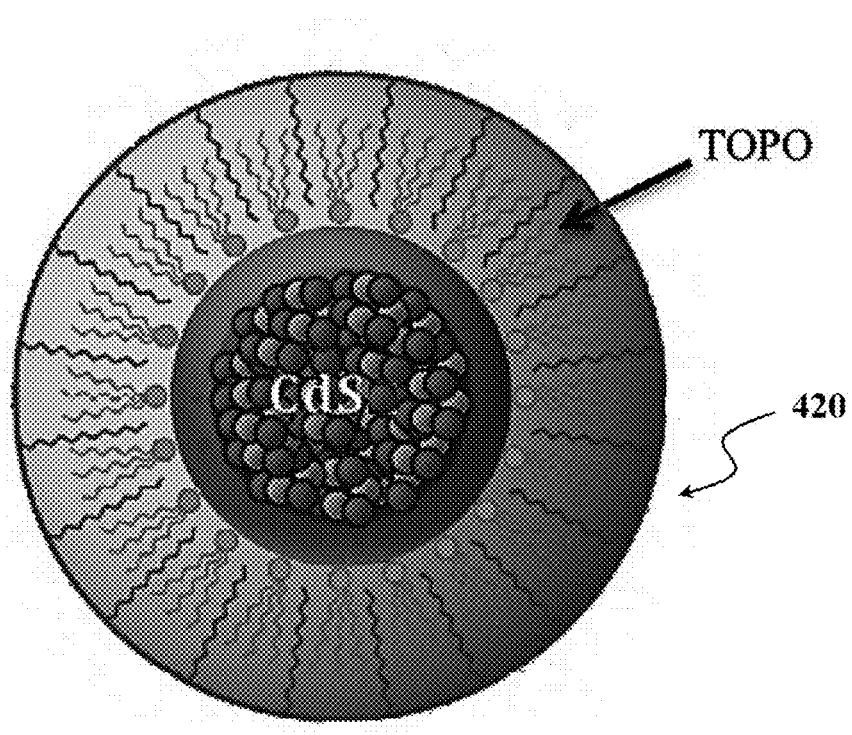

For purposes of clarity, referring to FIGS. 4A and 4B, two schematics of the CdS-TOPO QDs sorbent are provided. In FIG. 4A, an example of the CdS-TOPO chemical structure is illustrated. In FIG. 4B, an artistic rendering of the same is shown. As a general note, it can be seen that the CdS-TOPO QDs disk structure is similar to a kind of round structure or disk, with a plurality of CdS QDs and TOPO arranged across the surface of the disk. In this example, the CdS is arranged along the center while the TOPO is arranged around, or extends radially outward from, the CdS.

Figure 5:
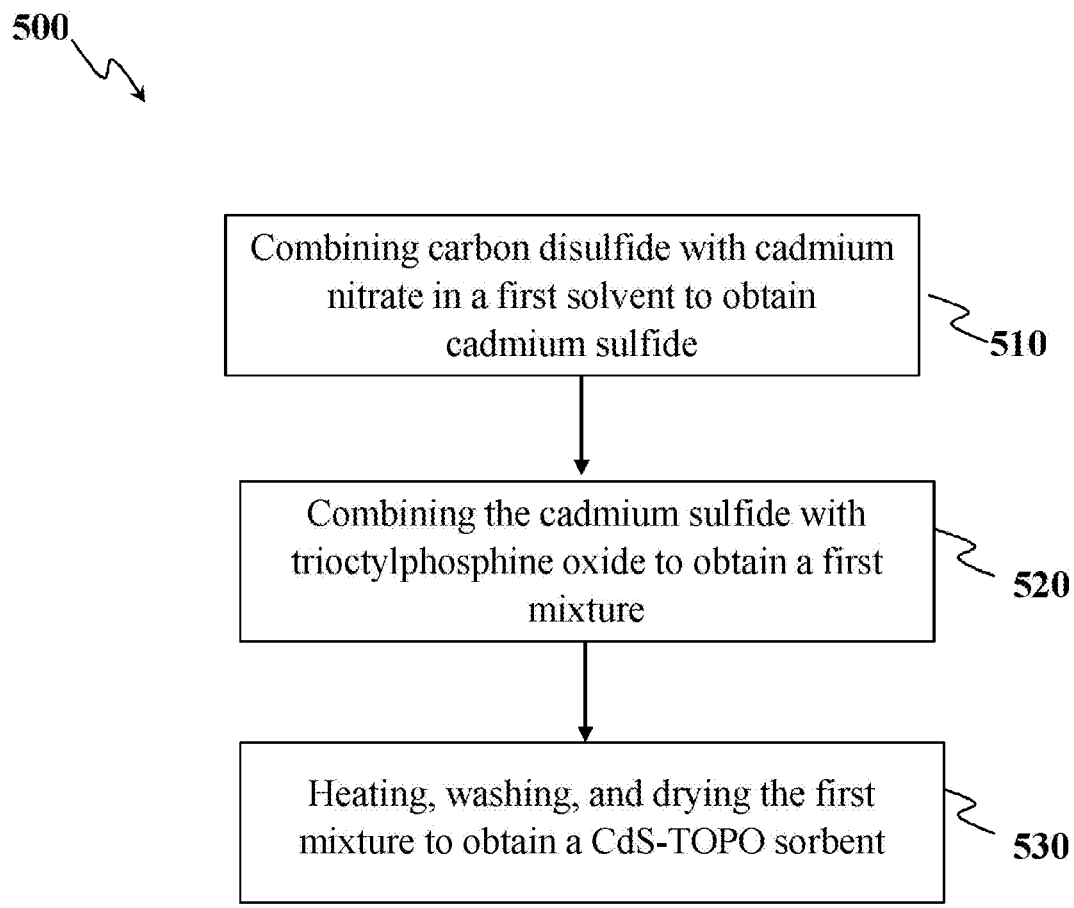
FIG. 5 is a flow chart depicting an implementation of a method of producing a CdS-TOPO QDs for application in the apparatus of FIGS. 1 and 2.

In order to better understand the characteristics of the CdS-TOPO sorbent illustrated in FIGS. 3 and 4, an implementation of a method of producing the sorbent is provided herein. Referring to flow chart presented in FIG. 5, a first step 510 includes combining carbon disulfide with cadmium nitrate in a first solvent, thereby forming cadmium sulfide. In one implementation, the cadmium sulfide is obtained as a powder that may include a white coloring. In a second step 520, the cadmium sulfide is combined, mixed, coated, or covered with the trioctylphosphine oxide, producing a first mixture. A third step 530 can involve heating the first mixture at a high temperature and obtaining a resultant powder that is washed and dried at room temperature, and produce what will be referred to herein as the CdS-TOPO composition or sorbent. In some implementations, the CdS-TOPO QDs sorbent can be heated in a steel reactor.

Figure 6:
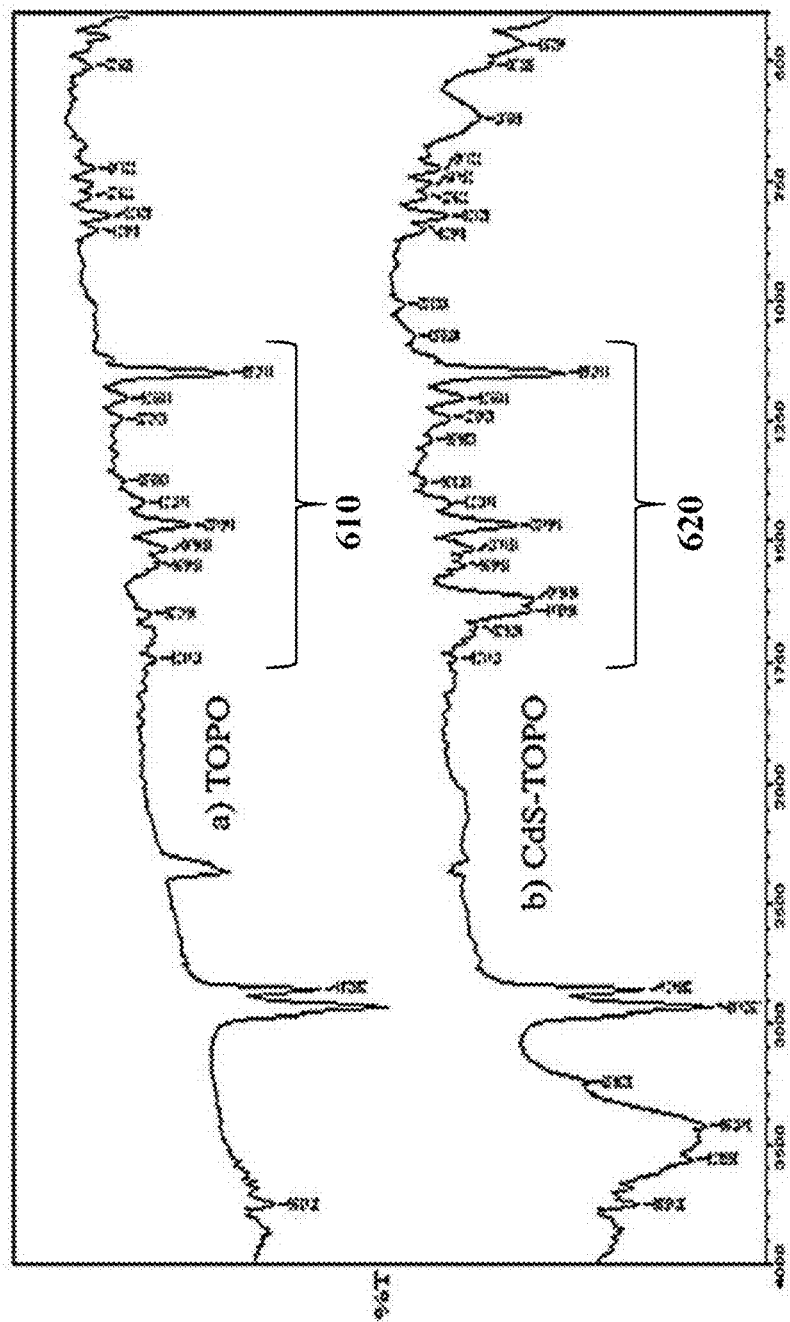
FIG. 6 presents an analysis of TOPO as well as CdS-TOPO QDs using (Fourier-Transform infrared spectroscopy) FT-IR, according to an implementation of the present disclosure.

Referring now to FIG. 6, an analysis of TOPO as well as the CdS-TOPO composition using (Fourier-Transform infrared spectroscopy) FT-IR is presented in, a graph. By comparing a first region 610 of TOPO with a second region 620 of CdS-TOPO, it can be understood that chemical bonding has occurred between the CdS and TOPO as a result of the first four steps of the method described above with respect to FIG. 5.

Figure 7:
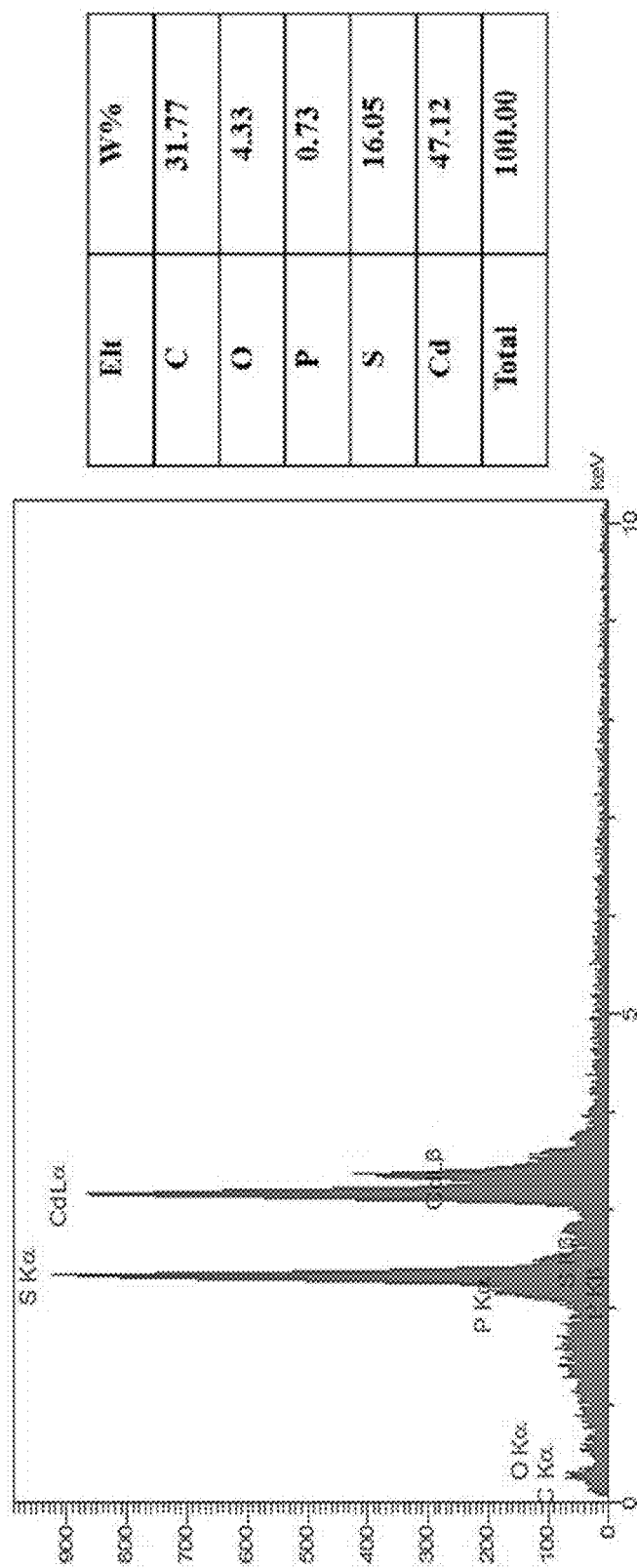
FIG. 7 presents an analysis of the CdS-TOPO QDs using (energy-dispersive X-ray spectroscopy) EDX, according to an implementation of the present disclosure.

Furthermore, for purposes of clarity, FIG. 7 presents an energy-dispersive X-ray spectroscopy (EDX) analysis of the CdS-TOPO composition and a chart presenting the measured results. Thus, FIG. 7 provides data with respect to the elements composition as well as an estimate of each element's relative abundance for an implementation of the composition.

Figure 8:
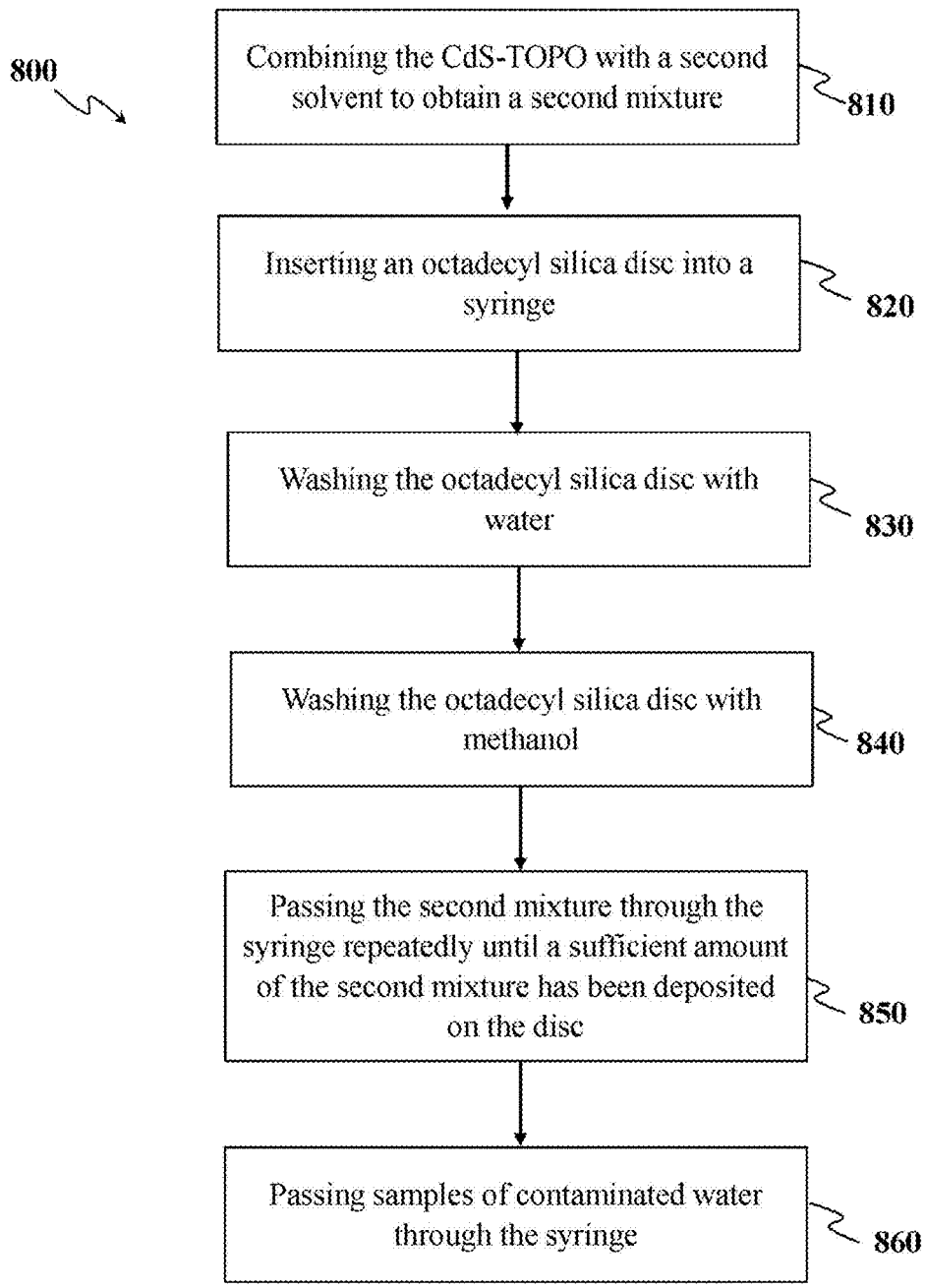
FIG. 8 is a flow chart depicting an implementation of a method of fabricating a CdS-TOPO QDs chemical filtration disk.

Referring next to FIG. 8, an implementation of a method of assembly of the filtration apparatus is described. A first step 810 includes combining or mixing the CdS-TOPO composition (see FIG. 5) with a second solvent to obtain a second mixture. In one implementation, the second solvent is toluene. In some other implementations, the second solvent can include aromatic hydrocarbons, methyl cyclohexane, acetates, and blends of ketones, esters, and/or alcohols and aliphatic hydrocarbons. In a second step 820 an ODS disk can be inserted into a syringe. In one implementation, the diameter of the disk can be substantially similar to the diameter of the syringe. In addition, as noted earlier, the disk can be sandwiched between other components in some implementations, and/or can be disposed within the housing. Thus, in one implementation, the disk can be part of a filter device unit, and the filter device itself is connected to the syringe in this step. While disposed in or connected to the syringe, a third step 830 can involve rinsing the disk with water. As an example, approximately 2 mL of water can be passed through the syringe to wash the disk positioned along the bottom portion of the syringe. In other implementations, the amount of water used in this step can vary. In a fourth step 840, the disk can be rinsed with methanol, or a chemical substance with similar properties. As an example, approximately 2 mL of methanol can be passed through the syringe to wash the disk positioned along the bottom portion of the syringe. In other implementations, the amount of methanol used in this step can vary. A fifth step 850 includes passing the second mixture through the syringe repeatedly until a sufficient amount of the second mixture has been deposited, arranged on, or adheres to the disk. Thus, the CdS-TOPO QDs can be passed through multiple times in order to obtain the desired chemical filter. The assembled syringe and filter device-unit can be referred to as a chemical filtration apparatus (see FIGS. 1 and 9). In different implementations, the filtration apparatus can then be dried, for example, in a vacuum. In addition, the disk can be washed to clear away excess QDs particles. At this time, the chemical filtration apparatus may be ready for use in measurement and extraction of particles.

Figure 9:
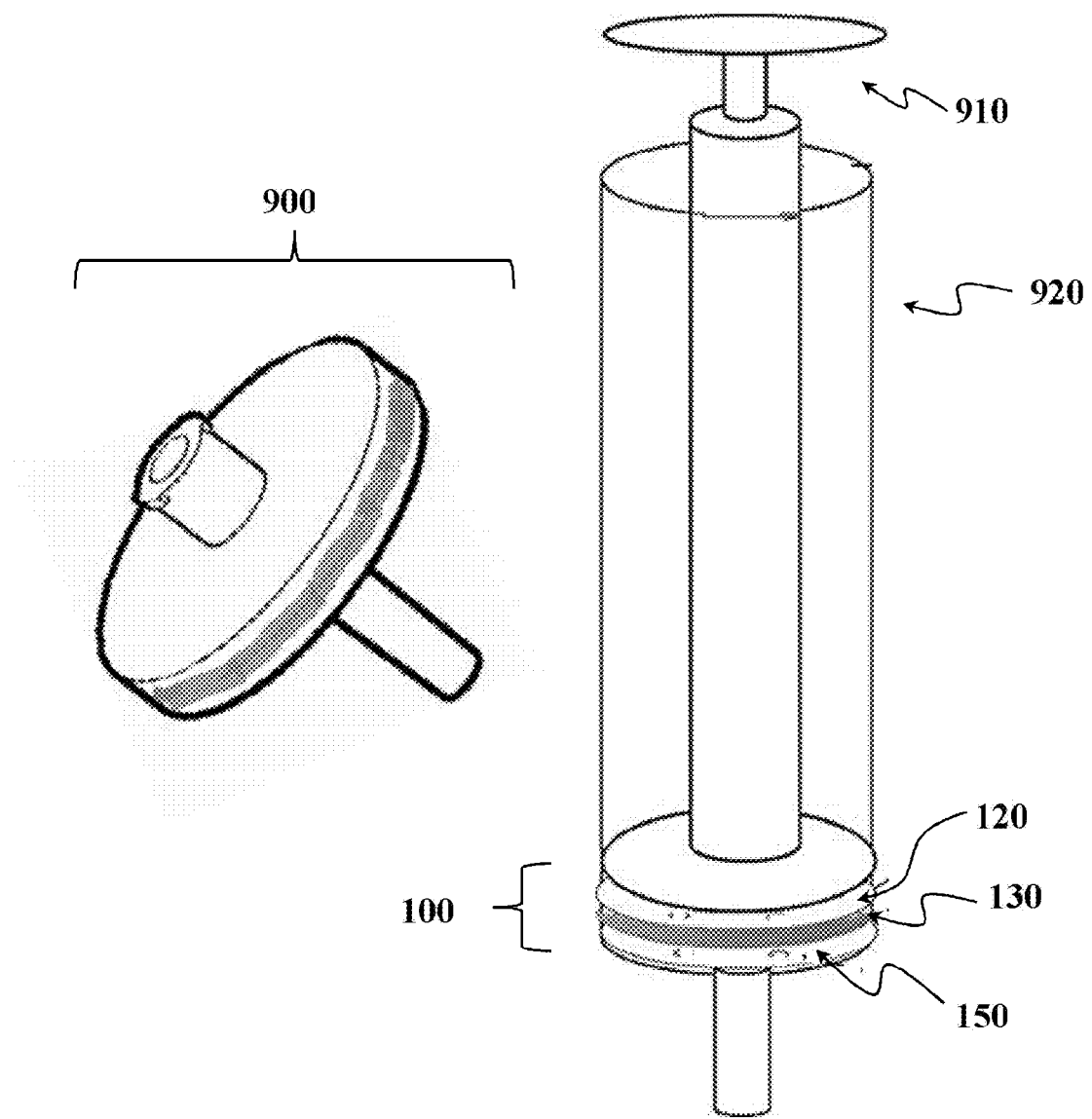
FIG. 9 depicts an isometric schematic view of an implementation of an apparatus for extraction of hydrocarbons.

In FIG. 9, an implementation of the assembled filtration apparatus 160 is illustrated, as well as a magnified view of a filtration unit 900, where the filtration unit 900 includes the filter device 100 encased in the housing. In some implementations, the housing can include a connector portion configured to allow insertion, connection, attachment, or securement of the filtration unit 900 to a syringe. The apparatus 160 further includes a plunger 910 associated with a syringe 920, which can be connected or attached to the filtration unit 900. The filter device, as discussed above with respect to FIG. 1, includes pre-filter 120, CdS-TOPO QDs disk 130, and disk support 150.

It should further be understood that in other implementations the apparatus may include other types of systems, such as an automated sample collection system in which contaminated fluid enters the system and is passed through a filter that includes the CdS-TOPO QDs composition (or other quantum dot-stabilizing agent) in order to extract the targeted molecules. This can ensure that the optimal conditions are maintained. For example, during testing of the apparatus, it was noted that a particular plunger compression velocity provided a maximum extraction efficacy. In some cases, an automated or mechanically operated system can better promote a consistent and uniform speed for the passage of fluid through the filter.

Example 1: Fabrication of a CdS-TOPO SPE Disk

For purposes of clarity, some details are provided with respect to the formation of a CdS-TOPO QDs filtration disk, according to an implementation of the present disclosure. However, it should be understood that in other implementations, one or more of the steps disclosed herein can be omitted as desired, or additional steps may be included. In one implementation, the method may include the formation of QDs through the colloidal synthesis technique. In this technique, nanocrystals are synthesized from solutions. Heating the solution at high temperature, the precursors decompose, forming monomers which then nucleate and generate nanocrystals.

In this following example, for a 1.5 cm piece of ODS disk, 5 mg of CdS-TOPO QDs was determined to provide optimal results. Different amounts of sorbent (3, 5, 10, and 15 mg) were examined and 5 mg was selected as the optimal amount in which the highest filter effectiveness and utility was found. Thus, a suspension of approximately 5 mg of CdS-TOPO particles was made in 1 mL of toluene. The suspension was then passed about 4-5 times through the ODS disk. During each pass, due to similar lipophilicity, a portion of suspended CdS-TOPO QDs became trapped in the pores and surface of the ODS disk. After these passes, substantially all of the CdS-TOPO QDs particles were transferred to the ODS disk, and the toluene solution had become clear. Thus, the number of passes was based on the determination that the substantially complete transfer of the particles had occurred.

Example 2: Characterization Tests

Figure 10:
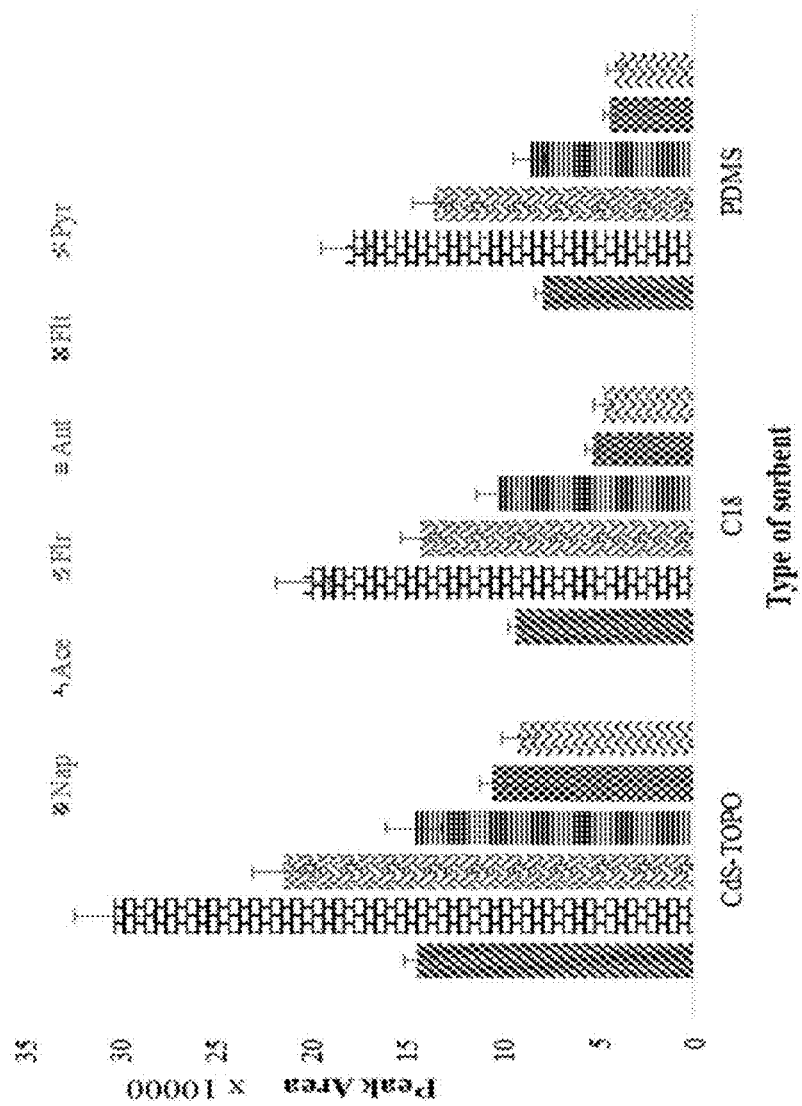
FIG. 10 provides a comparison of the effectiveness of the CdS-TOPO QDs sorbent relative to two general commercial sorbents, according to an implementation of the present disclosure.

Referring now to FIG. 10, the extraction performance of three different sorbent-based filters is presented for six aromatic agents, including naphthalene (Nap), acenaphthene (Ace), fluorene (Flr), anthracene (Ant), fluoranthene (Flt), and pyrene (Pyr). The six agents were selected in order to provide a diverse range across the spectrum of PAHs for testing. In the first section, the performance of the CdS-TOPO sorbent, as disclosed herein, with respect to these agents is shown. A second section illustrates the performance of a $C_{18}$-based sorbent, and a third section illustrates a PDMS-based sorbent. As shown in FIG. 11, it can be clearly seen that for each of the six agents, the CdS-TOPO sorbent extraction rate was significantly greater than that of either $C_{18}$ or PDMS.

Figure 11B:
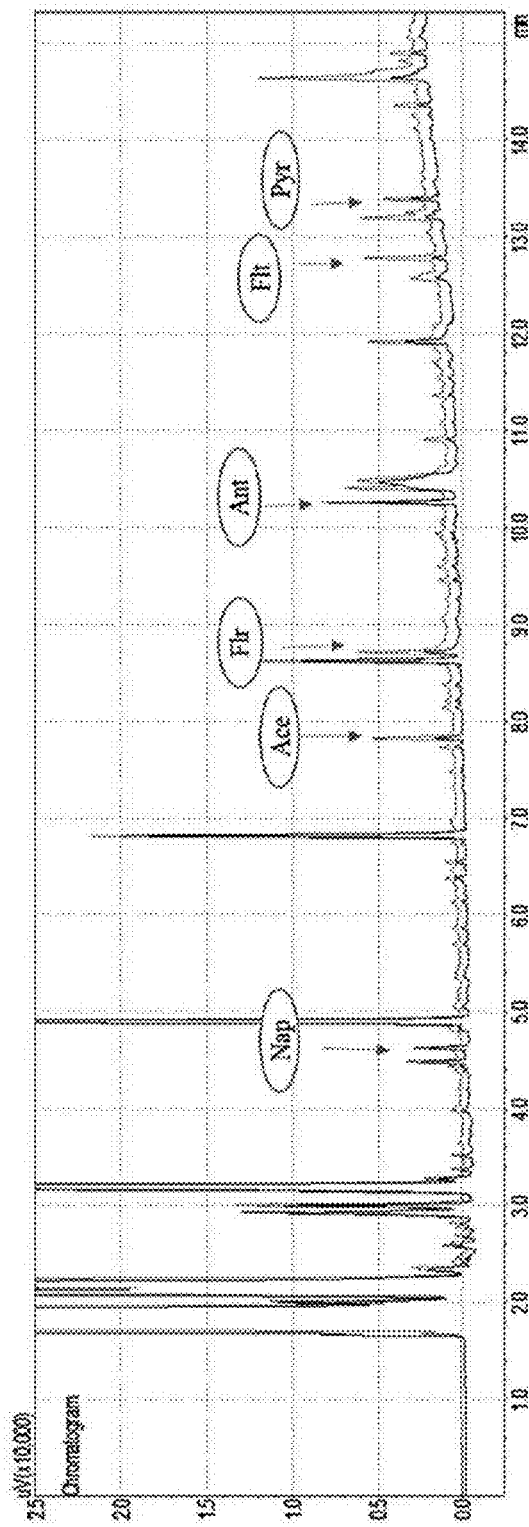

In FIGS. 11A-11C, results and analysis from a gas chromatography-flame ionization detector (GC-FID) are provided for the separation and measurement of the extracted analytes. FIG. 11A presents the parameters of selectivity, linearity, and LOD for the six selected analytes. In FIG. 11B, the lower graph curve represents the original extraction results taken from a sample of contaminated water. In other words, the chromatogram depicts the amount of pollutants on the filter disk after the chemical filtration process. It can be understood that each peak is associated with a polluting agent as identified on the graph. In order to verify the accuracy of the extraction filter, additional amounts of the six agents were added to the water, and a sample was tested again (see upper graph curve). As shown in FIG. 11B, there is a substantial similarity between the two graphs, confirming the accuracy of the apparatus during use. In addition, FIG. 11C presents the results from FIG. 11B in a table.

Thus, the SPE-disk-QD-TOPO tool disclosed herein provides high extraction efficiency, measurement accuracy, is relatively simple, low in cost, and has high potential for commercialization.

Example 3: Characterization Tests for Optimal Conditions

Figure 12A:
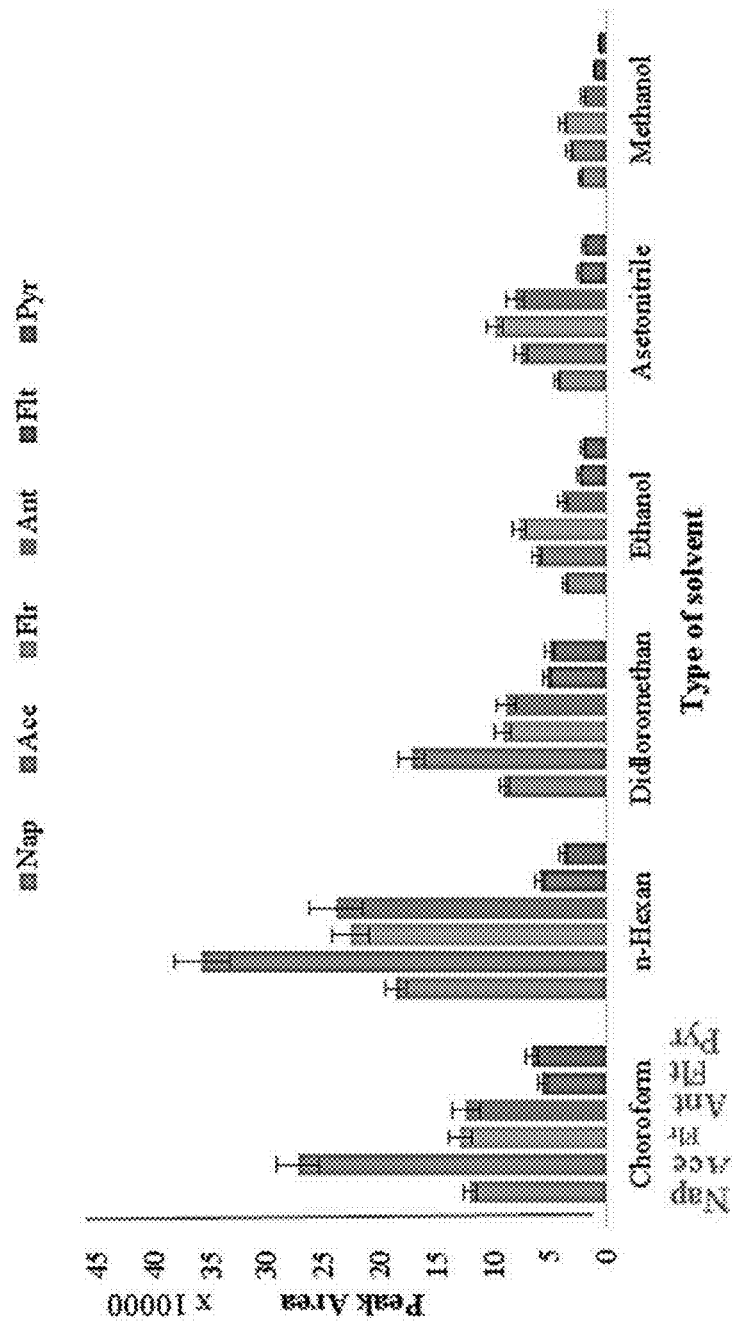
FIGS. 12A and 12B present two graphs reflecting the effect of the type and volume of the solvent used for the elution of the trapped PAHs from the CdS-TOPO QDs disk.
Figure 12B:
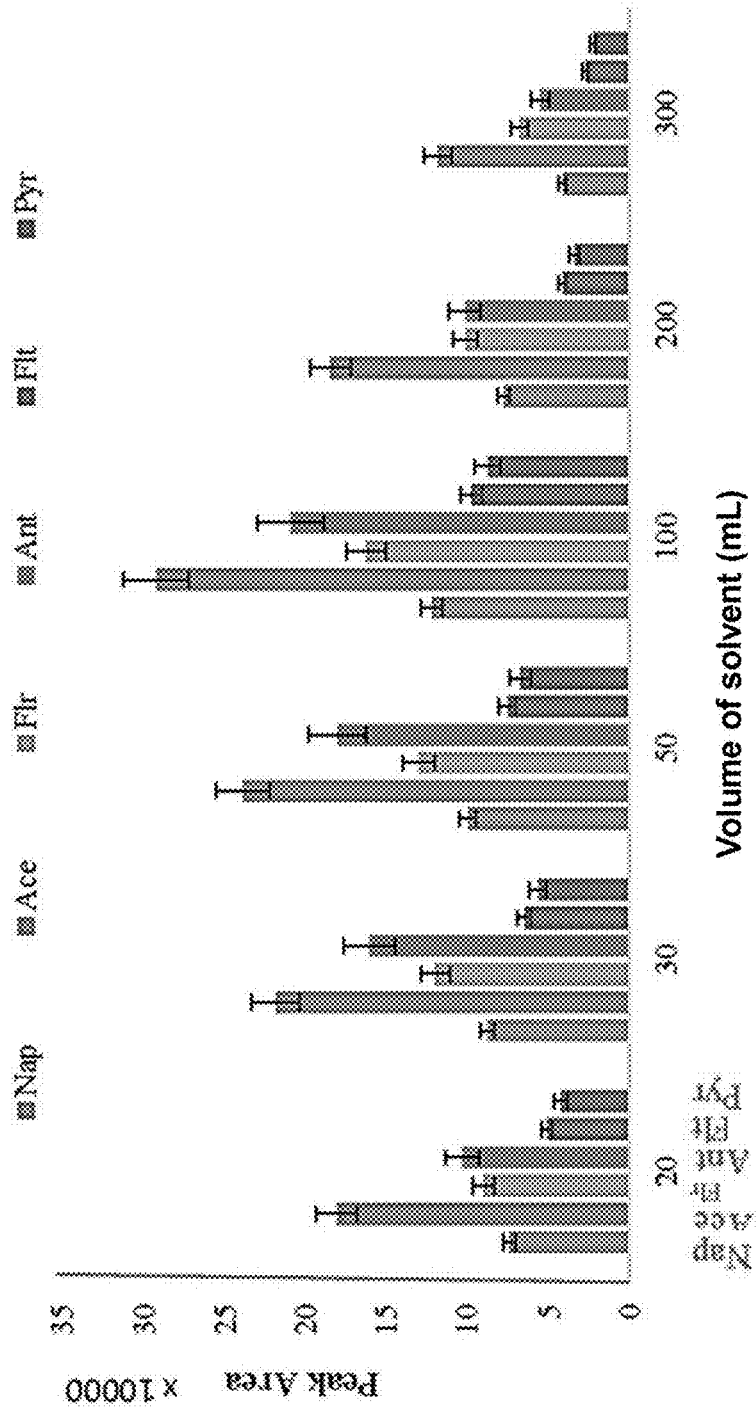

In FIGS. 12-14, additional data is provided reflecting the results of tests in which optimal conditions were determined. Referring to FIG. 12A, the effect of the type of solvent used (here, chloroform, n-hexane, dichloromethane, ethanol, acetonitrile, and methanol) and each solvent's relationship with the six different PAHs (naphthalene (Nap), acenaphthene (Ace), fluorene (Flr), anthracene (Ant), fluoranthene (Flt), and pyrene (Pyr)) is presented. Furthermore, in FIG. 12B, the volume of each solvent (the same as listed above) and its effects on the extraction of each PAH was tested.

Figure 13A:
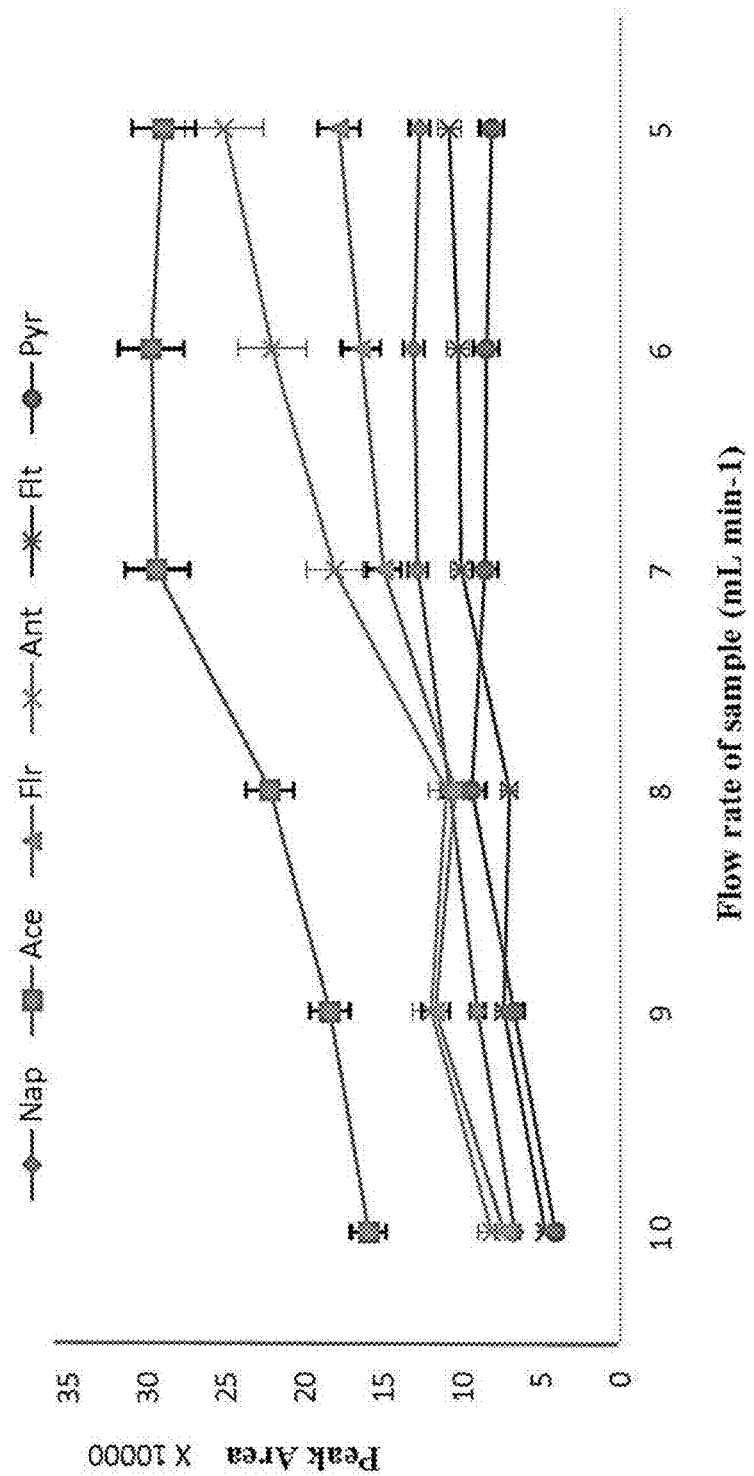
FIGS. 13A and 13B present two graphs indicating the effect of flow rate of the sample solution on the extraction efficiency and the effect of the flow rate of the elution solvent on the extraction efficiency.
Figure 13B:
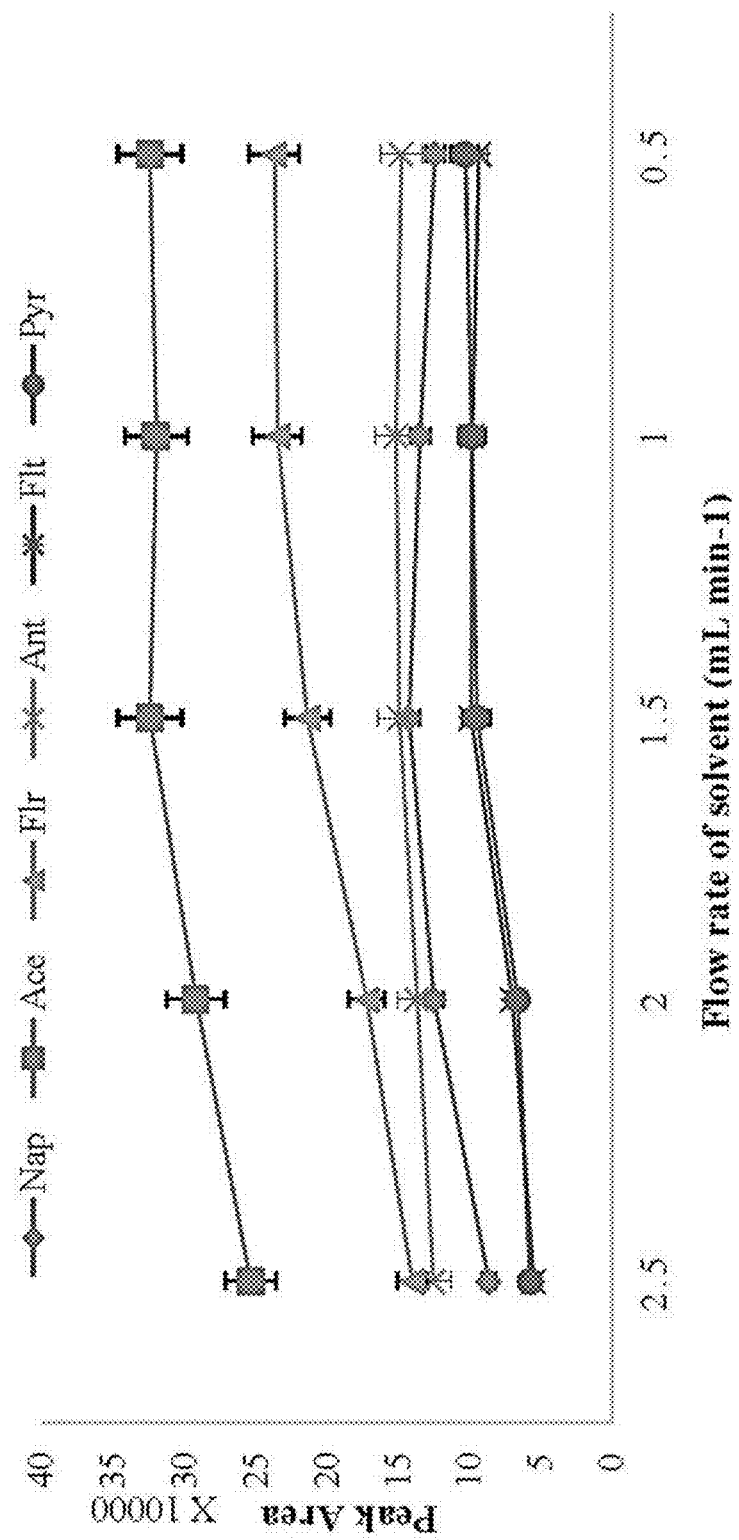
Figure 14A:
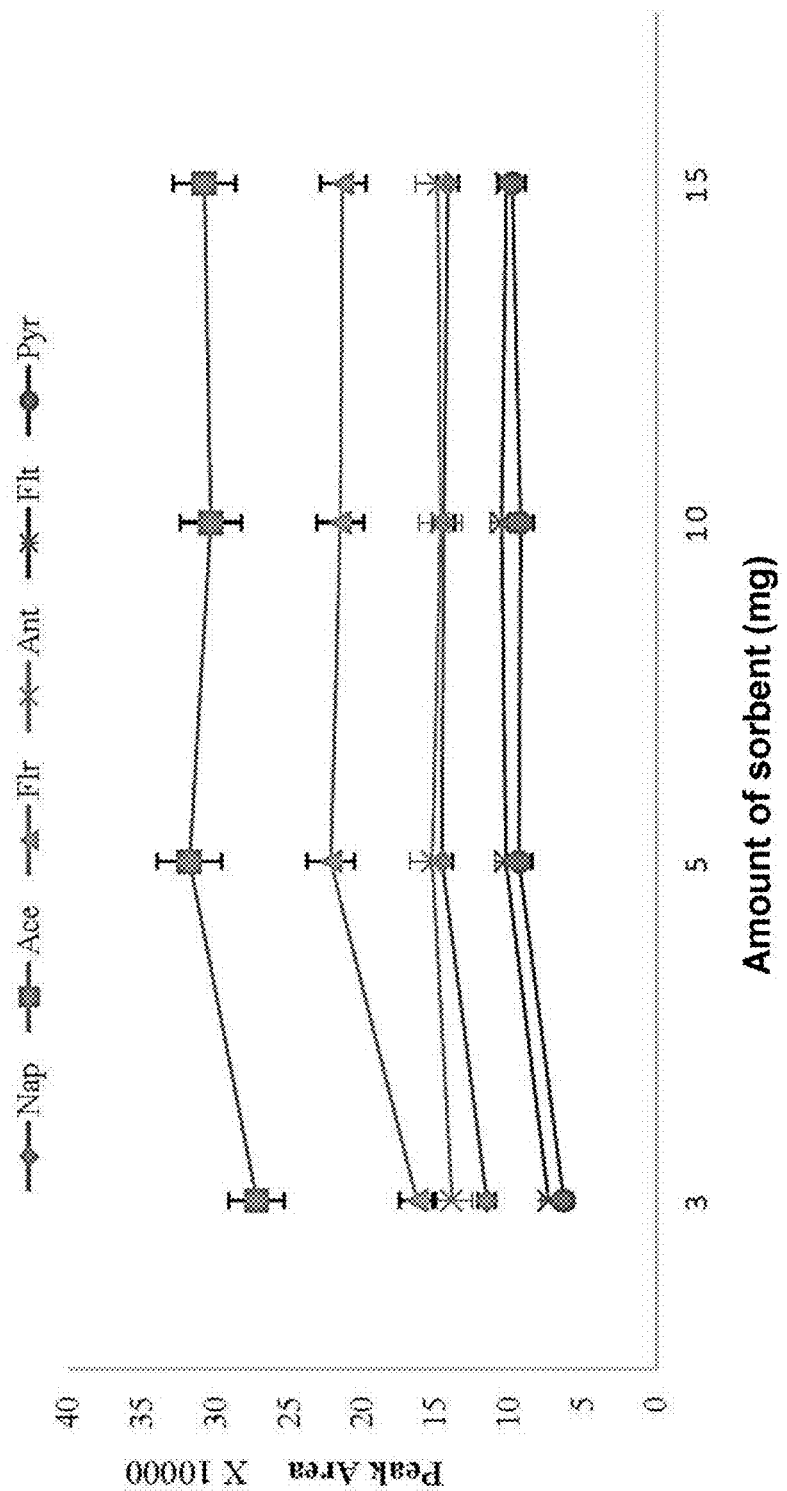
FIGS. 14A and 14B present two graphs showing the effect of the amount of sorbent and the volume of the sample on the extraction efficiency.
Figure 14B:
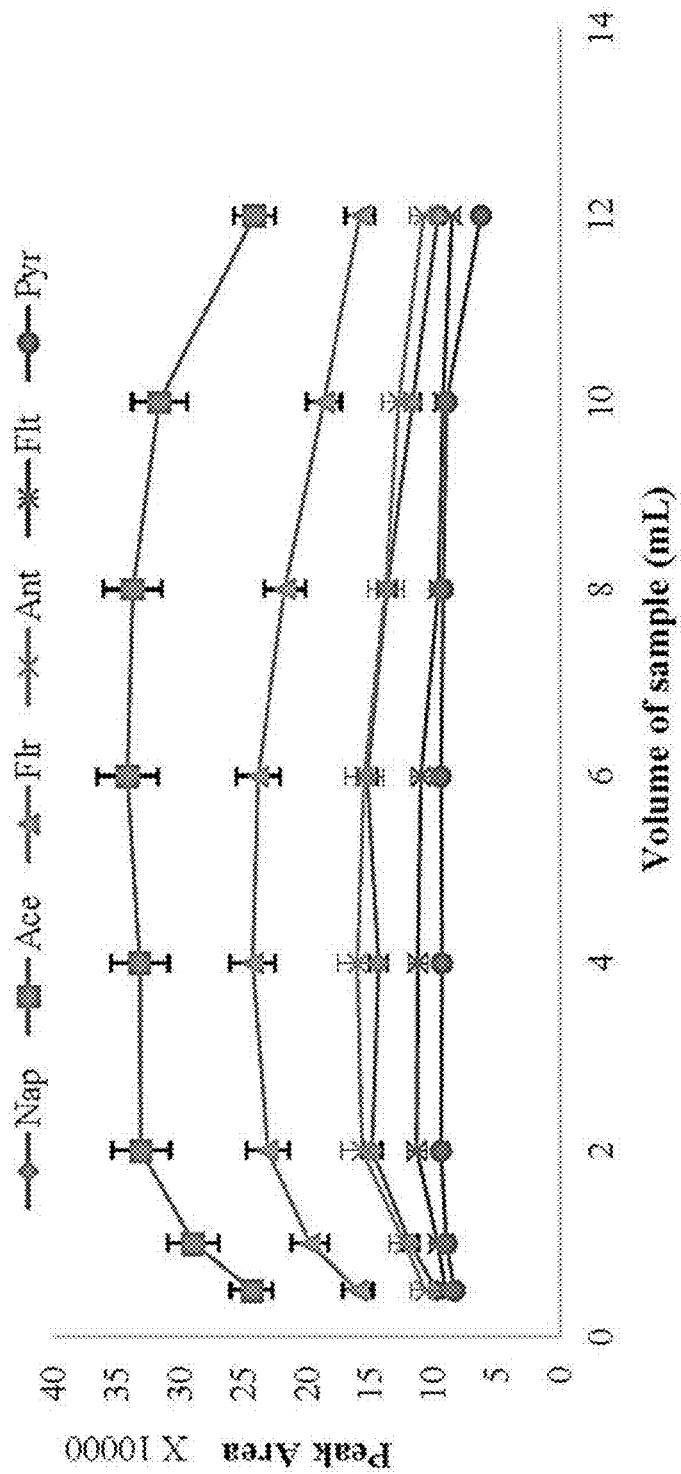

Furthermore, in FIG. 13A, the relationship of the flow rate of the sample with each of the six PAHs is presented, while in FIG. 13B the effect of the flow rate of the solvent on the extraction efficiency of each PAH is presented. Similarly, in FIG. 14A, the relationship of the amount of sorbent used on the extraction efficiency for each PAH is shown, and in FIG. 14B the effect of the volume of the sample on the extraction of each of the PAHs is shown.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which, they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for fabricating a filter disk, the method comprising:
   combining carbon, disulfide with cadmium nitrate in a first solvent, thereby forming a first mixture;
   producing cadmium sulfide (CdS) from the first mixture;
   adding trioctylphosphine oxide (TOPO) to the produced cadmium sulfide, thereby forming cadmium sulfide-trioctylphosphine oxide (CdS-TOPO) quantum dots;
   mixing the CdS-TOPO QDs with a second solvent to obtain a CdS-TOPO QDs mixture; and
   adding the CdS-TOPO QDs mixture to an ODS disk to form a filter disk.

2. The method of claim 1, further comprising:
   heating the first mixture at a high temperature and obtaining a resultant powder; and
   washing and drying the resultant powder to obtain the CdS-TOPO QDs.

3. The method of claim 1, further comprising inserting the ODS disk into a syringe.

4. The method of claim 3, further comprising:
   mixing the CdS-TOPO QDs with a second solvent to obtain a second mixture; and
   passing the second mixture through the syringe repeatedly until a first amount of the second mixture is deposited on a surface of the ODS disk.

5. The method of claim 3, further comprising washing the modified ODS disk with water and methanol.

6. The method of claim 4, further comprising:
   washing the filtration disk in order to clear away excess CdS-TOPO QDs disposed on the filtration disk; and
   drying the filtration disk.

7. The method of claim 3, wherein the ODS disk is disposed between a pre-filter and a disk support.

8. The method of claim 7, wherein the ODS disk, pre-filter, and the disk support are arranged in a housing that includes a connector portion configured to facilitate a connection with the syringe.

9. A filtration apparatus for extraction of polycyclic aromatic hydrocarbons, the apparatus comprising:
   a filter device, the filter device including a SPE disk; and a sorbent disposed on a surface of the SPE disk, the sorbent including a combination of quantum dot particles and a stabilizing agent.

10. The apparatus of claim 9, further comprising a filtration unit, the filtration unit including a housing, and the filter device being disposed within the housing.

11. The apparatus of claim 10, further comprising a syringe, and wherein the filtration unit is connected to the syringe.

12. The apparatus of claim 10, the filter device further comprising a pre-filter disk, wherein the SPE disk is positioned adjacent to the pre-filter disk.

13. The apparatus of claim 12, the filter device further comprising a disk support, wherein the SPE disk is positioned between the pre-filter disk and the disk support.

14. The apparatus of claim 9, wherein the SPE disk includes an ODS disk.

15. The apparatus of claim 9, wherein the quantum dot particles include cadmium sulfide.

16. The apparatus of claim 9, wherein the stabilizing agent includes trioctylphosphine oxide.

17. A method for extraction of polycyclic aromatic hydrocarbons, the method comprising:
   assembling a filter device, the filter device including a SPE disk covered with quantum dot particles and a stabilizing agent;
   drawing a sample fluid containing PAHs into a syringe;
   attaching a filtration unit to a syringe, the filtration unit including the filter device; and
   passing the sample fluid through the filter device.

18. The method of claim 17, wherein the SPE disk includes an ODS disk modified with CdS-TOPO QDs.

19. The method of claim 17, wherein the quantum dot particles include cadmium sulfide.

20. The method of claim 17, wherein the stabilizing agent includes trioctylphosphine oxide.

* * * * *